United States Patent [19]

Kolpak

[11] Patent Number: 4,852,395
[45] Date of Patent: Aug. 1, 1989

[54] THREE PHASE FLUID FLOW MEASURING SYSTEM

[75] Inventor: Miroslav M. Kolpak, Plano, Tex.

[73] Assignee: Atlantic Richfield Company, Los Angeles, Calif.

[21] Appl. No.: 281,421

[22] Filed: Dec. 8, 1988

[51] Int. Cl.⁴ ............................................. G01N 33/28
[52] U.S. Cl. .............................. 73/61.1 R; 73/861.04
[58] Field of Search ..................... 73/61 R, 61.1 R, 19, 73/53, 861.04

[56] References Cited

U.S. PATENT DOCUMENTS

| | | | |
|---|---|---|---|
| 3,246,145 | 4/1966 | Higgins | 73/61.1 R |
| 4,215,565 | 8/1980 | Vleck | 73/61.1 R |
| 4,395,902 | 8/1983 | Espenscheid et al. | 73/61 R |
| 4,429,581 | 2/1984 | Furmaga | 73/861.04 |
| 4,596,136 | 6/1986 | Zacharias | 73/61.1 R |
| 4,660,414 | 4/1987 | Hatton et al. | 73/61.1 R |
| 4,773,257 | 9/1988 | Aslesen et al. | 73/61.1 R |
| 4,776,210 | 10/1988 | Baillie et al. | 73/61.1 R |
| 4,788,852 | 12/1988 | Martin et al. | 73/61.1 R |

Primary Examiner—Hezron E. Williams
Attorney, Agent, or Firm—Michael E. Martin

[57] ABSTRACT

A multi-phase fluid flow measuring system for measuring the volumetric fractions of gas, water and oil including a centrifugal separator for conducting primary separation of gas from the liquid phase, a conduit section forming a closed chamber and a piston displaceable into the chamber to measure the increase in pressure of a liquid sample trapped in the chamber in relation to movement of the piston for determining the residual gas content of the liquid phase, a liquid phase flow meter and apparatus for measuring the microwave energy transmissivity through a sample of the liquid phase to determine the volumetric fraction of water and oil in the liquid phase. One embodiment of the system uses two apparatuses for measuring the microwave transmissivity at different pressures of the liquid phase to compare the transmissivity readings as a way of determining the residual gas content in the liquid phase. A method for measuring the residual gas content takes into consideration an increase in pressure in the sample of liquid being measured including elastic stretch of the measuring vessel as a result of the pressure increase, and compressibility of the liquid phase.

20 Claims, 4 Drawing Sheets

THREE PHASE FLUID FLOW MEASURING SYSTEM

BACKGROUND OF THE INVENTION

1. Field of the Invention

The present invention pertains to a three phase fluid flow measuring system including a centrifugal gas-liquid separator, a residual gas content measuring apparatus and a meter for determining the proportion of one liquid in another. The system is particularly useful for gas-water-oil mixtures being produced from underground reservoirs and the like.

2. Background

Efforts to measure the components of multi-phase fluid mixtures such as the gas-water-oil mixtures which are typically produced from oil and gas wells has resulted in the development of several types of flow measuring systems. For example, U.S. Pat. No. 4,776,210 to Lloyd A. Baillie et al and assigned to the assignee of the present invention describes a flow measuring system based on measurement of differential pressures and the measurement of the dielectric constant of the water-oil mixture separated from the gas fraction of the flowstream. Although this type of system is useful in relatively large steady state flowstreams it is not particularly attractive for use with small intermittent flowstreams such as often result from the production of fluids from individual wells.

In many oil and gas operations it is important to be able to measure the components of a multi-phase fluid flowstream produced from each well in n oil or gas well field. However, a system which is adaptable for measuring the intermittent and widely varying range of the components of a multi-phase fluid stream such as is typically produced by wells in a reservoir which is under various stimulation techniques, there is a need for a relatively low cost, simple yet effective system which is capable of measuring the volumetric flow of each component of the flowstream for various reasons including the adjustment of stimulation techniques and the allocation of net production volumes to those wells which may be owned by more than one party. It is to this end that the present invention has been developed with a view to providing an effective, compact and relatively uncomplicated flow measuring system which is particularly adapted for measuring the components of a gas-water-oil mixture of the type typically encountered in the production of underground hydrocarbon reservoirs.

SUMMARY OF THE INVENTION

The present invention provides an improved flow measuring system for measuring multi-phase fluid flow, including fluid flow streams of gas-water-hydrocarbon liquid mixtures including crude oil and natural gasoline liquids produced from underground reservoirs.

In accordance with an important aspect of the present invention a system is provided which includes an uncomplicated yet effective centrifugal type gas-liquid separator, an apparatus for measuring the residual gas content of the liquid flowstream, an apparatus for measuring the amount of each liquid in the liquid mixture separated from the gas and together with flow measuring apparatus for measuring the total liquid flow stream and the total gas flowstream after separation.

In accordance with another aspect of the present invention a multi-phase fluid flow measuring system is provided which includes in improved apparatus and method for measuring the residual gas content in a liquid mixture which has undergone primary gas-liquid separation processes. In particular, the residual gas content measurement device includes a piston which displaces a particular amount of fluid in a closed chamber wherein the change in pressure in the chamber and its effect on deflection of the structure defining the chamber and the compressibility of the liquid is taken into consideration.

The present invention still further provides improved flow measuring systems for measuring a multi-phase fluid flowstream emanating from a well wherein the flow rate of the fluid flowstream varies considerably as well as the proportion of the various components of the flowstream varies considerably. Various other features of the respective embodiments of the invention described herein will be further appreciated by those skilled in the art upon reading the detailed description which follows in conjunction with the drawing.

DESCRIPTION OF PREFERRED EMBODIMENTS

Figure 1:
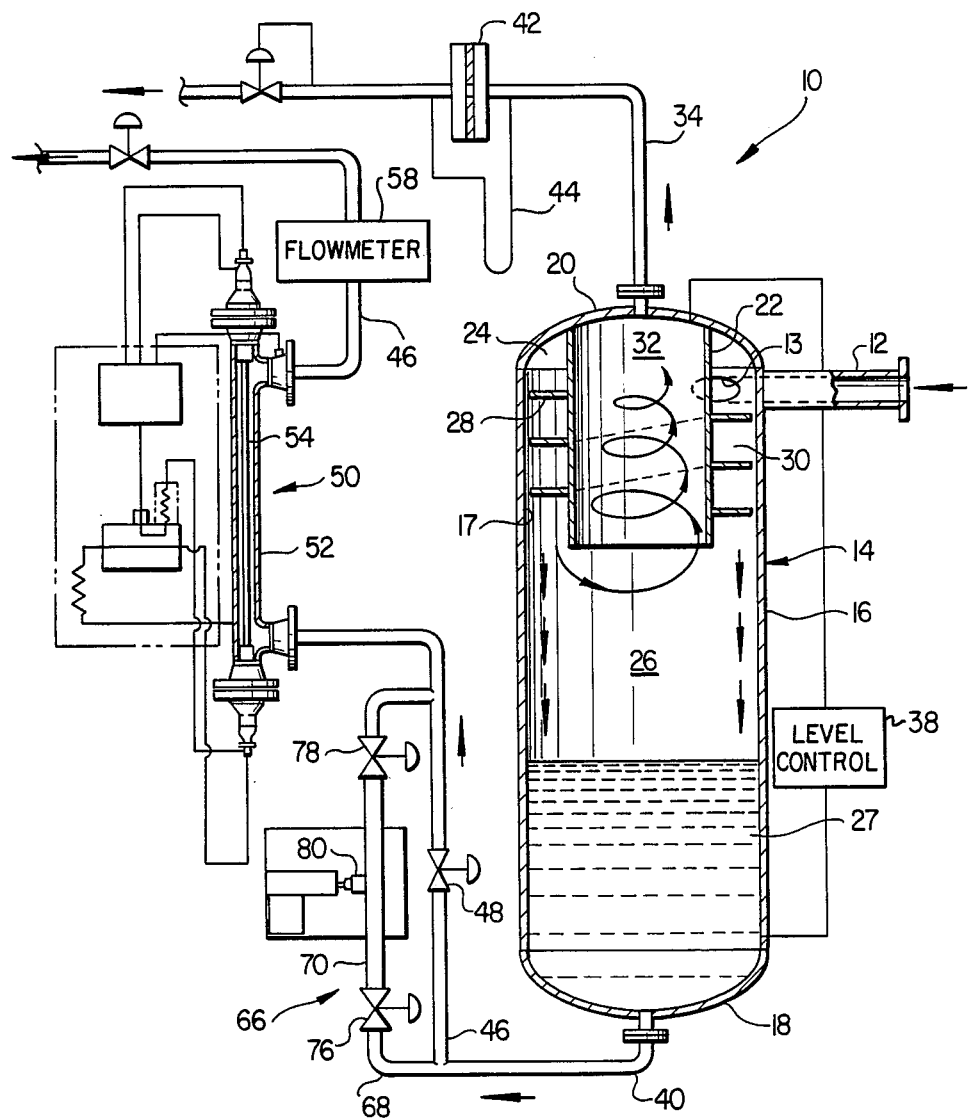
FIG. 1 is a schematic diagram of a multi-phase fluid flow measurement system in accordance with the present invention.

In the description which follows like parts are generally marked throughout the specification and drawing with the same reference numerals, respectively. The drawing figures are not necessarily to scale and certain features are shown in schematic form in the interest of clarity and conciseness.

Certain crude oil reservoirs throughout the world produce fluids which comprise basically a mixture of a gas and a liquid mixture of water and oil. Oil fields that are being stimulated by gas or water drive, in particular, may produce widely varying rates of one component of such a three phase mixture as compared with the other components of the mixture. It is important in the development an production of at least certain oil fields to be able to monitor the composition of the fluid flowing from each well rather than gathering the fluid streams and analyzing the production of several wells collectively. In this regard it is important to be able to have in-circuit with each well production fluid flow conduit a flow measuring system which is relatively compact, structurally simple and inexpensive but yet accurate to within a few percent of measurement of the gas content as well as the water and oil content of the liquid mixture in the flowstream.

FIG. 1 is a schematic diagram of an improved fluid flow measuring system particularly adapted for the aforementioned applications. Referring to FIG. 1 there is illustrated a fluid flow measuring system 10 which includes a centrifugal or cyclone type separator of improved construction and which receives the inlet flow stream from a well or the like through an inlet conduit 12. The separator illustrated in FIG. 1 is generally designated by the numeral 14 and comprises a generally cylindrical housing or shell 16 having bottom and top head portions 18 and 20. A generally cylindrical internal baffle 22 depends from the head portion 20 and forms an annular space 24 as part of an interior chamber 26 defined by the separator housing or shell 16. The annular chamber 24 is provided with a spiral plate baffle 28 which is wound around and secured to the baffle 22 and forms a spiral duct 30 which opens from the chamber 24 into the chamber 26.

The spiral baffle 28 preferably extends radially to within a fraction of an inch of the side wall 17 of the shell 16 to facilitate assembly and disassembly. The conduit 12 opens into the chamber 24 in a tangential manner along the side wall 17 by way of an opening 13. Accordingly, the fluid mixture entering the separator 14 undergoes a cyclonic or spiral descending flow path through the space 30 whereby the more dense liquid is flung against the wall 17 and trickles down this wall into the chamber 26. The fluid flowstream entering the chamber 26 at the outlet of the spiral flow path or duct 30 is flowing in a vertical manner which further separates any liquid from the gas flow stream and the gas then flows upward through a chamber portion 32 formed within the baffle 22 and through a gas outlet flow conduit 34. The liquid separated from the gas occupies the lower portion of the chamber 26 and the level of liquid in this portion of the chamber, as indicated by the numeral 27, may be controlled by a level control means 38 operable to control a remotely operated flow control valve, not shown, in the inlet conduit 12. Residence time of the liquid in the chamber 26 may be controlled to allow further separation of gas bubbles still entrained in the liquid whereupon the liquid then exits the separator 14 through a flow conduit 40.

It has been determined that a relatively simple pressure vessel made of suitable pressure vessel grade steel may be constructed for handling flows in the range of 3,000 barrels of liquid per day mixed with approximately 3,000,000 standard cubic feet of gas per day. A separator having a shell diameter of approximately 2.0 feet by an overall height of 5.0 feet would occupy a relatively small space at a well site but yet appears to be capable of effectively separating from 90 to 95% of the gas in the flowstream on a volumetric basis. Moreover, the structure of the separator 14 is relatively uncomplicated, relying on conventional pressure vessel construction techniques and with a relatively uncomplicated yet effective internal baffle system characterized by the cylindrical depending baffle 22 and the single spiral plate type baffle 28 which forms the spiral or helical duct or flow passage 30.

Referring further to FIG. 1, the gas separated from the flowstream in the separator 14 is conducted by way of the conduit 34 through a suitable gas flow measuring means such as an orifice meter comprising an orifice 42 and a pressure differential measurement device 44. Conventional gas flow measurement processes and apparatus such as the orifice meter 42 may thus be used to measure the gas content of the flow stream and the gas may be either remixed with the liquid flowstream or conducted to a suitable gas handling facility, not shown.

The liquid being conducted through the conduit 40 may, on a steady state basis, be conducted through a continuing conduit portion 46 having a shutoff valve 48 interposed therein. The conduit 46 is connected to an apparatus, generally designated by the numeral 50, which is adapted to measure the composition of the liquid mixture utilizing electrical properties such as the dielectric constant of the liquid mixture. In particular, the apparatus 50 includes a housing forming a through flow conduit portion 52 in which a microwave conductor element 54 is disposed in the form of an elongated rod. The apparatus 50 is of a type which measures electromagnetic radiation transmissivity in the microwave frequency range through a combined water-oil liquid mixture for measurement of the water fraction in the liquid mixture. The apparatus 50 is preferably of a type described in U.S. patent application Ser. No. 06/932,068 filed Nov. 18, 1986 in the name of Bentley N. Scott and Y. Sam Yang and assigned to the assignee of the present invention. In particular, the apparatus 50 includes an oscillator circuit whose operating frequency changes in accordance with the concentration of one liquid in the mixture in relation to the mixture and the frequency change may be affected by the residual gas content of the liquid mixture. This frequency change or a change in the transmissivity of microwave energy may be correlated with the dielectric properties of the fluid mixture. Similar devices of somewhat less accuracy and lacking some of the unique features of the apparatus 50 and also of a known type may be substituted for the apparatus 50 for determining the water and oil fraction of the liquid mixture. For example, a device known as a Water Cut Monitor and available from Halliburton Company, Dallas, Tex. may be substituted for the device 50 and for the sake of this discussion the device 50 may comprise such a measuring apparatus.

The total volumetric flow of the liquid mixture may also be measured with a conventional Coriolis or positive displacement flowmeter of a type commercially available and generally designated by the numeral 58. The liquid mixture, after conduction through the flowmeter 58, may be conducted further through the conduit 46 to a suitable liquid handling facility for separation of the oil from the water, for example.

Figure 2:
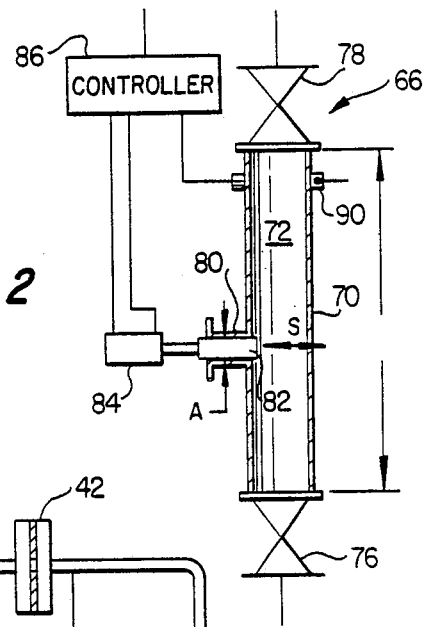
FIG. 2 is a schematic diagram of a residual gas content measurement device for the system of the present invention.

The separation of all of the gas from the liquid mixture is difficult to obtain by the separator 14, particularly while considering the maintenance of a suitably small size of the separator which does not permit long residence time of the primarily separated liquid in the chamber 26. Accordingly, in order to correct any errors in readings from the apparatus 50 and meter 58 it is important to provide further separation of gas or to measure the gas content which is residual in the liquid mixture. An important aspect of the present invention is determining the residual gas content of the liquid mixture so that readings of the flowmeter 58 can be corrected to account for the gas content. In this regard the system illustrated in FIG. 1 includes a residual gas content measuring device 66 which is interposed in a branch conduit 68 connected to the conduit 46 to form a bypass around the valve 48. The device 66 includes an elongated conduit 70, see FIG. 2 also, which forms an interior chamber 72 which is generally cylindrical in configuration and devoid of any pockets or portions which may trap unwanted quantities of gas or liquid. The conduit 70 is connected at its opposite ends to remotely controllable shut off valves 76 and 78. The conduit 70 includes a branch portion 80 which intersects the main portion of the conduit 70 and journals a reciprocable piston 82 disposed therein and adapted to project into the chamber 72. The normal retracted position of the piston 82 is such that little if any space is provided in the branch conduit portion 80 for occupancy by fluid and therefore no gas may normally be trapped in the conduit 70 before and during pressure tests to determine the residual gas content of the fluid flowstream.

The piston 82 is adapted for control to extend and retract with respect to the chamber 72 by an actuator 84 which is operable to be controlled by a suitable controller device 86. The controller device 86 is also suitably connected to a pressure transducer 88 to measure the change in the chamber 72 in relation to the position of the piston 82. A device which works in some ways similar to the residual gas content measuring device 66 is disclosed in U.S. Pat. No. 4,329,869 to Toda. Furthermore, the device 66 may also include suitable temperature sensing means 90 for measuring the temperature of the fluid flowing through the chamber 72 and any change therein resulting from a change in pressure of the fluid as influenced by movement of the piston 82.

The system 10 is operable to measure total liquid flow continuously by the flowmeter 58, total gas flow continuously by the flowmeter 42 and the percentage of water in oil liquid or vice versa by continuous measurement using the apparatus 50 to measure the transmissivity of microwave radiation. Moreover, these flows may be corrected for the amount of residual gas in the liquid flowstream flowing through the conduit 46 by periodic batch sampling of a quantity of liquid with residual gas therein by closing the valve 48 and opening the valves 76 and 78 long enough to trap a representative sample of liquid in the chamber 72, then simultaneously closing the valve 76 and 78 and reopening the valve 48 to prevent build-up of liquid in the chamber 26. When a quantity of liquid with some residual gas entrained therein is trapped in the chamber 72 the piston 82 may be stroked to penetrate into the chamber 72 a predetermined distance while measuring the corresponding change in pressure inside the chamber 72 to determine how much free gas is present in the liquid stream. For example the following equation may be used to determine the gas fraction (fg) when it is expected that the gas fraction is less than 10% of the total volume of the fluid in the chamber 72:

$$fg = (A.s)/[(1 - P1/P2)(V_s)] \quad (1)$$

wherein: A equals the cross sectional area of the piston 82, s equals the piston penetration or stroke into the sample in the chamber 72, P1 is the sample pressure before the piston activation, P2 is the pressure after the piston activation and $V_s$ is the batch sample volume including the liquid and gas.

It may be determined that the increase in temperature of the sample for a gas fraction of about 10% or less is insignificant and thus the process is essentially isothermal allowing the use of the ideal gas laws. However, certain corrections should be included for elastic stretch of the conduit 70 under the effect of the increasing pressure in the chamber 72, the redissolving of some of the gas into the liquid and the compressibility of the liquid. When the piston 82 (of area A) is stroked (by distance s) into the sample in the chamber 72, the sample volume is decreased by as and the pressure increases. Each fluid component shrinks. Conservation of volume implies the following about fluid volumes in the cylinder before and after the piston stroke:

$$dV = V2 - V_s \quad (2)$$

where
V2 = fluid volume after the piston stroke,
dV = fluid volume change = $G \cdot V_s \cdot dP - A \cdot s$,
G = an elastic stretch factor of the volume of the space 72 due to stretch or expansion of the conduit 70 and dp = P2 − P1.
V2 is the sum of individual component volumes $$V2 = V_o' + V_w' + V_g' \quad (3)$$

where the primes denote shrunken volumes immediately after the pressure increase and the notations o, w and g denote oil, water and gas, respectively. Expressions for each of these terms are listed below:

$$V_g' = (fg - fgr) \cdot V \cdot [P1/P2] \cdot [Z2/Z1] \quad (4)$$

$$V_o' + V_w' = (1 - fg) \cdot V_s \cdot e^{-b \cdot dP} \quad (5)$$

where
fgr = gas fraction re-dissolved due to dP,
Z1,Z2 = gas compressibility factors at P1 and P2,
b = liquid compressibility coefficient, and
e = constant 2.71828

The compressibility factors Z1 and Z2 may be obtained from the Gas Processors Suppliers Assn., Engineering Data Book, Ninth edition. Substituting in equations 3 and 2, and rearranging, yields the working equations:

$$fg = \frac{[A.s/V_s] - dP.(b + G) - fgr'}{1 - dP.b - [P1/P2].[Z2/Z1]} \quad (6)$$

in which fgr' is an abbreviation of the product of terms $$fgr \cdot [P1/P2] \cdot [Z2/Z1] \quad (7)$$

and in which $e_{-b.dP}$ is approximated by 1 − b.dP; since b.dP << 1.

The value of the re-dissolving term, fgr, must be less than or equal to fg. Moreover, fgr is expected to be much less than fg (say, 1% of fg) because the re-dissolving process will be limited by the finite gas-liquid interfacial area, and because the pressure increase and measurement will be administered quickly; in a few seconds. The product of terms, fgr', will therefore likely be small enough to ignore. Regardless of its size, the effect of fgr' will be to slightly reduce the pressure increase and to cause a slight overestimation of gas fraction, fg.

As the residual gas content or gas fraction (fg) of the liquid sample approaches zero the pressure will increase rapidly if the piston 82 is stroked when gas content is very small. For fg=0 and fgr=0, equation (6) yields:

$$dP = (A.s/V_s)/(b + G) \quad (8)$$

The piston 82 should not be stroked far if gas content of the fluid is near zero; otherwise overpressuring the components of the device 66 will result.

As the residual gas content (fg) increases, pressure will increase relatively slowly as the piston 82 is stroked. In the limit fg=1, fgr=0, ignoring G because of its small relative value, and equation (6) yields:

$$dP/p1 = (Z2/Z1)/[1-(A.s/Vs)]-1 \qquad (9)$$

A relatively large stroke is needed to produce a measurable effect on pressure. As the effect becomes measurable, say 1%, the Z2/Z1 factor will differ slightly from unity and it can be expressed as a function of the initial pressure, temperature and the differential pressure increase. On the basis of the above the operation of the device 66 should be controlled such that the pressure in conduit 70 should not be raised more than a few percent; so as to keep the "re-dissolving error", (fgr'), as small as possible. Since the gas fraction (fg) may be anywhere in the 0 to 10 range, and knowledge of even its approximate value should not be assumed, the piston 82 should be stroked in two stages. For example, initially stroke the piston 82 into chamber 72 a very short distance so as not to overpressure the valve seals in the event the gas fraction is near zero. Then, if the initial pressure increase did not exceed 5%, advance the piston 82 until 5% is achieved and compute the gas fraction (fg) via equation (6).

A resolution of 0.5% in estimating fg via equation (6) should be sufficient for flowmetering purposes. For example, fg=0.015±0.005. Tests indicate accuracies of ±0.001. Thus approximate values (from textbooks) of the compressibility coefficient (b) and the stretch factor (G) of conduit 70 can be used in equation (6).

Moreover, it should also be possible to measure the compressibility of the liquid phase by stroking the piston 82 until pressure rises by 100 psi or more, and then stroke the piston 82 again until pressure rises by another 100 psi.

This provides two sets of piston stroke(s) and pressure change (dP) data which can be substituted into equation (6) to solve simultaneously for (fg) and compressibility coefficient (b). The value of (b) should then be regarded as the compressibility of the liquid phase, from which we may solve for oil fraction (fo) and water fraction (fw) as follows:

$$fo + fw = 1 - fg \qquad (10)$$

$$fo.bo + fw.bw = b \text{ (liquid phase compressibility coefficient value)} \qquad (11)$$

$$\text{from which: } fw = \frac{b - bo(1-fg)}{bw - bo} \qquad (12)$$

where
b,fg=values determined from equation (6) and
bo,bw=compressibility coefficients of the oil and water in the sample, respectively.
Values of the compressibility factors bo and bw can be measured by the piston/cylinder unit itself, by periodically sampling from layers of oil and water from a small settling tank.

A computer controlled linear actuator 84 should have no difficulty in stepping through as many stroking stages as might be necessary to measure gas fraction and liquid compressibility with reasonable accuracy.

Figure 3:
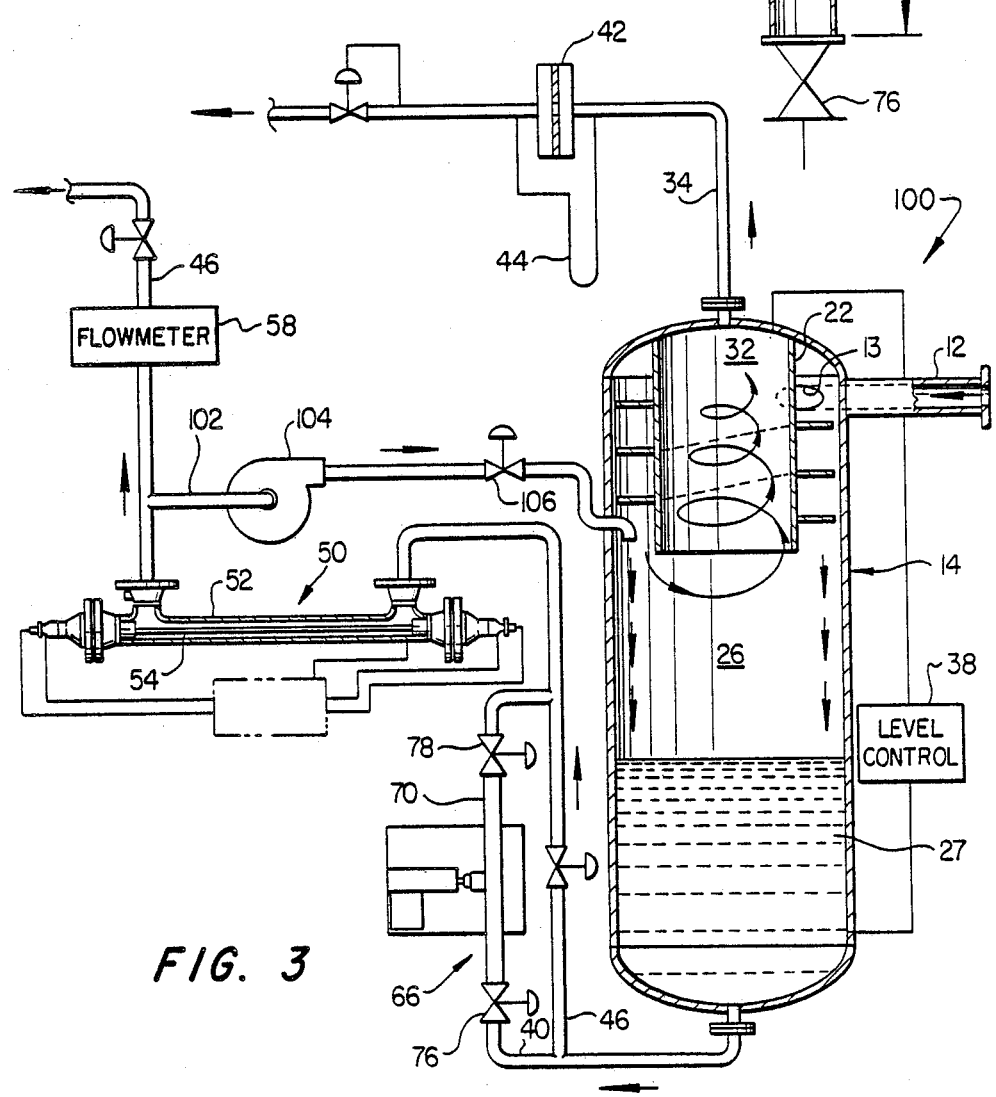
FIG. 3 is a schematic diagram of a first alternate embodiment of a system in accordance with the present invention.

Referring now to FIG. 3, there is illustrated a modification of the system illustrated in FIG. 1 and which is designated by the numeral 100. The system 100 is similar to the system 10 in essentially all respects except for the inclusion of a return conduit 102 which is connected to the conduit 46 and includes interposed therein a recirculating pump 104 and a throttling valve 106. The conduit 102 is connected to the separator vessel 14 for recirculating some of the liquid flow back to the separator vessel for use in certain applications of a system in accordance with the present invention wherein severe disruptions in the liquid flow occur or an extremely high percentage of gas is present. The system 100 may, in fact, be used as a so called well test system for determining the exact specifications of a system which would measure the flow rate on a continuous or production basis.

Figure 4:
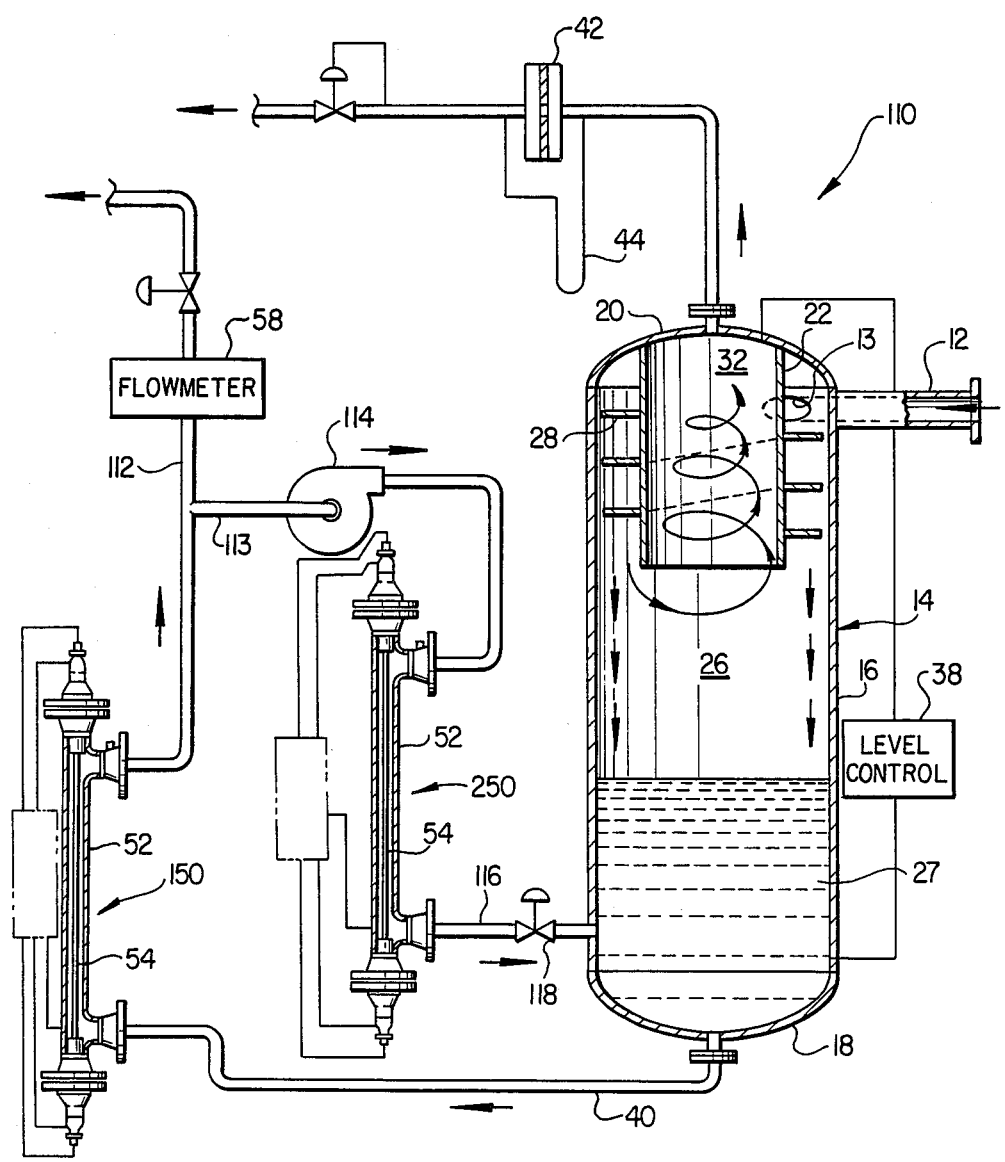
FIG. 4 is a schematic diagram of a second alternate embodiment of a system in accordance with the present invention.

Referring to FIG. 4, there is illustrated a second alternate embodiment of a system for measuring multiphase fluid flow rates in accordance with the present invention. The system illustrated in FIG. 4 is designated by the numeral 110 and includes a separator vessel 14, a gas flow rate measuring meter 42 interposed in a gas outlet conduit 34 and an outlet conduit 40 for conducting substantially gas free liquid from the separator vessel. The conduit 40 is connected to the inlet of an apparatus 150 identical to the apparatus 50 for measuring the fraction of oil in water or vice versa, the outlet of which is in communication by way of a conduit 112 with a flowmeter 58. A second apparatus 250 also identical to the apparatus 50 is provided in the system 110 in communication with the conduit 112 by way of a branch conduit 113 and a pressure boosting pump 114 and is connected to the separator vessel 14 by way of an outlet conduit 116 having a suitable throttling valve 118 interposed therein.

The arrangement of the system 110 is such that the residual gas content of the liquid flowing through the conduit 40 may be determined by reading the transmissivity of microwave radiation through the apparatus 150 interposed in the conduit 40 and comparing the reading of the apparatus 150 with the reading taken from the apparatus 250 at a higher pressure as provided by the pump 114. By circulating liquid through the conduit 40 and the branch conduit 113, 116 by way of the pump 114 a comparison of the measurements taken by the two apparatuses 150 and 250 can indicate the residual gas content in the liquid flowstream. For example by providing a pump 114 having a small capacity of about 5.0 to 10.0 gallons per minute pressure may be boosted for the fluid entering the apparatus 250 downstream of the pump to shrink the gas bubbles that may be present in the liquid flow stream and thus the two apparatuses 150 and 250 will register slightly different readings of the dielectric constants of the fluid flowing therethrough.

The flow rates for the respective fractions of oil, water and gas may be determined from the following. Since the pressure boost is small, the ideal gas laws may be used.

$$fg2 = fg1[P/(P+dP)] \qquad (A1)$$

where (fg1,fg2) are volumetric gas fractions in the apparatus 150 and 250 respectively, P is the pressure in apparatus 150, and dP is the pressure boost achieved in apparatus 250. Equation (A1) is modified to account for some of the free gas (fgr) re-dissolving in the liquid.

$$fg2 = fg1[P/(P+dP)] - fgr \qquad (A2)$$

As discussed previously, fgr is expected to be less than 1% when dP/P is on the order of 0.05 or less.

The volumetric liquid fractions (ff) and gas fractions (fg) are related as follows (the numerals 1 and 2 refer to the conditions in the apparatus 150 and 250, respectively):

$$ff1 + fg1 = 1 \quad (A3)$$

$$ff2 + fg2 = 1 \quad (A4)$$

$$ff2/ff1 = (1 - fg2)/(1 - fg1) \quad (A5)$$
$$= (1 + fgr - Pr.fg1)/(1 - fg1)$$

where $Pr = P/(P+dP) = P1/P2$.

In apparatus 250, the gas fraction will be lower, and therefore the liquid fraction will the compensatingly higher, than in apparatus 150 by the factor ff2/ff1. However, the water-to-oil ratio will be identical in both apparatus 150 and 250. Therefore the oil fraction (fo) and the water fraction (fw) in apparatus 250 will both be higher by the same factor ff2/ff1 (fw)

$$fo2 = fo1(ff2/ff1) \quad (A6)$$

$$fw2 = fw1(ff2/ff1) \quad (A7)$$

The mixture dielectric constants or microwave transmissivity factors (E1,E2) registered by the two apparatuses 150 and 250 can be expressed in terms of the oil, water and gas dielectric constants (eo,ew,eg) and volumetric fractions (fo,fw,fg) as follows:

$$fo1.eo + fw1.ew + fg1.eg = E1 \quad (A8)$$

$$fo2.eo + fw2.ew + fg2.eg = E2 \quad (A9)$$

These dielectric constants may be considered in terms of the frequency at which the oscillator circuits of the apparatuses 150 and 250 operate for a particular mixture composition at the respective operating pressures.

Substituting equations (A1), (A5), (A6) and (A7) into (A9) yields $$(ff2/ff1).[fo1.eo + fw1.ew] + Pr.fg1.eg - fgr.eg = E2 \quad (A10)$$

Combining equation (A10) with equation (A8) yields the solution for the gas fraction (fg1)

$$fg1 = \frac{E2 - E1(1 + fgr) + eg(fgr)}{E2 - E1(P1/P2) + eg(1 - P1/P2)} \quad (A11)$$

Substituting (A11) in (A8) and utilizing the continuity equation:

$$fo1 + fw1 + fg1 = 1 \quad (A12)$$

yields the following solution for oil fraction $$fo1 = \frac{(ew - E1) + (ew - eg).fg1}{(ew - eo)} \quad (A13)$$

The oil volumetric flow rate Qo is obtained from $$Qo = Q.fo1 \quad (A14)$$

where Q is the total volumetric flow rate from the flowmeter 58

Figures 5, 6:
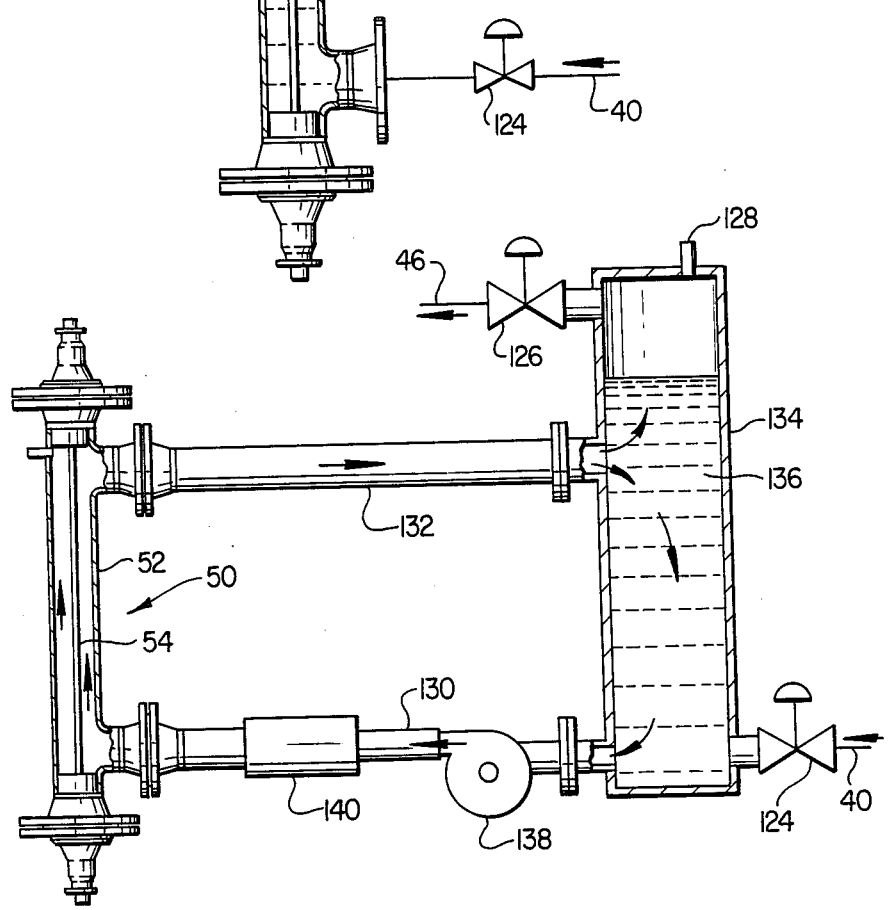
FIG. 5 is a schematic diagram of a portion of the system of FIG. 1 modified to provide for separation of residual gas from the liquid mixture.
FIG. 6 is a schematic diagram of another embodiment of a component for separating the residual gas in the liquid mixture.

Referring to FIG. 5 there is illustrated yet another embodiment of the present invention wherein an apparatus 350 is adapted to be interposed in the liquid discharge conduit 40 from the separator vessel 14 in place of the device 66 and the apparatus 50 in the system 10, for example. The apparatus 350 is essentially the same as the apparatus 50 but is also utilized to measure the residual gas content in the liquid by allowing a quantity of the liquid to enter the apparatus and reside therein until the residual gas fraction separates from the liquid fraction. In the modification of the invention illustrated in FIG. 5 the apparatus 350 includes an outer housing or conductor 120 forming a chamber 122 for receipt of a quantity of liquid which has undergone primary gas separation. The conduit 120 is adapted to receive a liquid sample in the chamber 122 through an inlet valve 124 and discharge a sample through a valve 126 connected to the conduit 46 and flowmeter 58 (see FIG. 1). The center conductor 54 extends through the chamber 122 in the same manner as described earlier herein. The conduit 120 is arranged generally vertically so that residual gas entrapped in the liquid sample may separate and collect at the top of the chamber 122 wherein a suitable liquid level sensing device 128 is disposed for determining the liquid level in the chamber 122. Accordingly, a liquid sample may be trapped in the chamber 122 and allowed to reside a sufficient length of time to permit separation of the residual gas. Then readings of the dielectric strength of the liquid sample in the chamber 122 may be made to determine the fraction of water and oil and correcting for the now known amount of gas in the chamber 122. By knowing the residual gas content of the liquid sample the flowmeter 58 may be corrected for any errors in reading the flow rate therethrough.

Accordingly, the steps of measuring the flow rates and gas fraction using the modified system of FIG. 5 would be to conduct flow through the apparatus 350 to flush a previous sample, isolate a sample in the chamber 122 by closing the valves 124 and 126 and allowing the residual gas to segregate in the upper part of the chamber 122 and then measure the height of the gas column to determine the percent by volume of the gas in the sample. The fraction of water and oil may then be obtained by taking readings of the microwave radiation transmissivity or dielectric strength of the fluid in the chamber 122. These steps would provide sufficient information regarding all three components of the multiphase fluid flowstream.

FIG. 6 illustrates a further modification of the system of FIG. 5 wherein an apparatus 50 is interposed in supply and return branch conduits 130 and 132 which are connected to a column type vessel 134 in which the liquid sample is allowed to reside sufficiently long to allow gas to collect at the top of a chamber 136 as illustrated. Sample shut off valves 124 and 126 are interposed in the system to trap the sample of liquid with residual gas interposed therein and liquid may be circulated through the apparatus 50 by a pump 138 and a suitable mixing device 140 to assure a homogeneous mixture of liquid to be measured by the apparatus 50. A liquid level sensor 128 is also provided for the sample vessel 134 to determine the percent by volume of the fluid sample which is liquid and gas, knowing the volume of the chamber 136. The system of FIG. 6 provides for thoroughly homogenizing the liquid free of any residual gas to more accurately determine the oil and water fraction.

Although preferred embodiments of a system and method for measuring the volumetric flow rate of a multi-phase fluid flowstream have been disclosed herein those skilled in the art will recognize that various substitutions and modifications may be made to the system without departing from the scope and spirit of the invention as recited in the appended claims.

What is claimed is:

1. A system for measuring multi-phase fluid flow including a water-oil-gas mixture comprising:
    conduit means for conducting a multi-phase fluid flow stream;
    separator means connected to said conduit means for separating the liquid phase of said fluid flowstream from the gas phase, said liquid phase having a residual gas content said separator means including a gas outlet conduit and a liquid outlet conduit;
    gas flow rate measuring means interposed in said gas outlet conduit;
    means for measuring the residual gas content of a liquid flowstream leaving said separator means through said liquid outlet conduit; and
    means for measuring the fraction of one liquid in another in said liquid flowstream leaving said separator means through said liquid outlet conduit.

2. The system set forth in claim 1 wherein:
    said separator means comprises a separator vessel including means for inducing a cyclonic flow of said fluid flowstream.

3. The system set forth in claim 2 wherein:
    said separator vessel includes spiral baffle means for receiving said fluid flowstream from said conduit for inducing said cyclonic flow of said fluid flowstream, said baffle comprising a single spiral plate and a generally cylindrical member depending from one end of said vessel, said spiral plate disposed around said cylindrical member and projecting radially outwardly the within a small distance of the wall of said vessel.

4. The system set forth in claim 1 wherein:
    said means for measuring the residual gas content of said liquid flowstream includes a sampling apparatus including a generally cylindrical conduit section, valve means at opposite ends of said conduit section operable to be closed to define a closed chamber in said conduit section, a piston adapted for reciprocal movement into said chamber a predetermined amount, and means for measuring a pressure increase in said chamber in relation to the movement of said piston to determine the change in volume as compared with the increase in pressure to measure the volumetric fraction of residual gas remaining in the liquid of a sample of fluid trapped in said conduit section.

5. The system set forth in claim 1 wherein:
    said means for measuring the fraction of one liquid in another comprises a conduit section including microwave frequency range conductor means including a portion of said conduit section and means for conducting microwave radiation through said conduit section and said conductor means for determining the fraction of one liquid in another by the change in microwave transmissivity through said conduit section in the presence of said liquid mixture.

6. The system set forth in claim 1 where:
    said means for determining the residual gas content of said liquid flowstream includes a first apparatus including a first liquid conduit through which liquid is conducted and microwave frequency range conductor means including a portion of said first liquid conduit for determining the fraction of one liquid in another at one pressure condition of said liquid flowstream, and a second apparatus including a second liquid conduit through which liquid is conducted and microwave frequency range conductor means including a portion of said conduit section for determining the fraction of one liquid in another at a pressure different from the pressure of the liquid being conducted through said first apparatus whereby by comparing the attenuation of microwave radiation transmissions through said first and second apparatus the gas content of said liquid phase may be determined.

7. The system set forth in claim 1 including:
    volumetric flow measuring means interposed in said liquid outlet conduit for measuring the volumetric flow rate of liquid.

8. The system set forth in claim 5 wherein:
    said conduit section includes means for holding a quantity of liquid to allow residual gas to separate from said liquid and means for measuring the level of liquid in said conduit section after separation of said gas.

9. The system set forth in claim 1 including:
    branch conduit means interconnecting said liquid outlet conduit and said separator means, pump means interposed in said branch conduit means for returning at least a portion of the liquid flowstream to said separator means during periods of relatively high gas to liquid flow ratios of said flowstream entering said separator means.

10. A method for measuring the volumetric flow rate of a multi-phase fluid flowstream including a gas phase and a liquid phase and wherein said liquid phase includes a mixture of at least two liquid compositions, said method comprising the steps of:
    separating said gas phase from said liquid phase in primary separation means;
    measuring the flow rate of gas leaving said primary separation means;
    conducting the liquid phase having a residual gas content from said primary separation means to means for measuring the residual gas content of said liquid phase;
    measuring the change in pressure of a known initial volume of a quantity of said liquid phase with residual gas therein in relation to a volumetric displacement of a piston in said means for measuring the residual gas content to determine the residual gas content in said liquid phase;
    measuring the fraction of at least one liquid composition in said mixture; and
    measuring the volumetric flow rate of said liquid phase.

11. The method set forth in claim 10 including:
    determining the elastic stretch of said means for measuring the residual gas content in response to said change in pressure and comparing the volume change of said means for measuring the residual gas content due to said elastic stretch with the volume change of said known initial volume of said quantity of liquid phase due to the volumetric displacment of said piston.

12. The method set forth in: claim 11 including the step of:
    determining the gas fraction of the residual gas content of said quantity of said liquid redissolved in said liquid due to said change in pressure for determining the volume of said gas in said quantity of said liquid.

13. The method set forth in claim 12 including the step of:

determining the gas compressibility factors at an initial pressure of said quantity of said liquid and at the pressure due to said change in pressure of said quantity of liquid and determining the volumetric fraction of said quantity of liquid which is gas (fg) from the equation:

$$fg = \frac{[A.s/V_s] - dP.(b + G) - fgr'}{1 - dP.b - [P1/P2].[Z2/Z1]}$$

wherein A is the cross sectional area of said piston, s is the stroke length of said piston, $V_s$ is the initial volume of said quantity of liquid, dP is the change in pressure due to the volumetric displacement of said piston into said means for measuring the residual gas content, b is the liquid compressibility coefficient, G is the elastic stretch factor of said means for measuring the residual gas content, fgr' is the gas fraction redissolved in the liquid due to the change in pressure, P1 is the initial pressure, P2 is the pressure after displacement of said piston, Z1 is the gas compressibility factor at the initial pressure and Z2 is the gas compressibility factor at the pressure after volumetric displacement of said piston.

14. The method set forth in claim 13 including the step of:

increasing the pressure during an initial volumetric displacment of said piston by not more than about 5 of the initial pressure of said quantity of liquid prior to determining the gas fraction (fg) from the equation of claim 13.

15. The method set forth in claim 13 including the step of:

determining the compressibility of said quantity of said liquid by displacing said piston in said means for measuring until the pressure increases at least approximately 100 psi while measuring said volumetric displacement of said piston followed by displacing said piston an additional volumetric displacement to obtain a further increase of pressure of said quantity of liquid in said means for measuring and determining the fraction of one liquid (fw) of said liquid wherein:

$$fw = \frac{b - bo(1 - fg)}{bw - bo}$$

wherein bw is the compressibility coefficient of said one liquid in said mixture and bo is the compressibility coefficient of the other liquid in said mixture.

16. The method set forth in claim 15 including the step of:

measuring the compressibility coefficient of said liquid compositions in said mixture.

17. The method set forth in claim 10 including:

providing means for collecting a sample of the liquid phase to permit separation of residual gas in the liquid phase and measuring the volume occupied by the liquid phase and the separated residual gas in said sample.

18. A method for measuring the volumetric flow rate of a multiphase fluid flowstream including a gas phase and a liquid phase and wherein said liquid phase includes a mixture of at least two liquid compositions, said method comprising the steps of:

separating said gas phase from said liquid phase in a primary separation means:

conducting said liquid phase having a residual gas content from said primary separation means to means for measuring the residual gas content of said liquid phase comprising a first apparatus including a first conduit section through which said liquid phase is transmitted and including means for measuring the transmission of microwave radiation through said first conduit section at a first pressure of said liquid phase flowing through said first conduit section, and conducting said liquid phase to a second apparatus including a second conduit section and means for measuring the transmissivity of microwave radiation through said second conduit section at a second pressure of said liquid phase greater than said first pressure; and comparing the change in microwave transmissivity in said first conduit section and said second conduit section to determine the volumetric fraction of gas in said liquid phase.

19. The method set forth in claim 18 including the step of:

providing pump means interposed in a conduit connecting said first apparatus and said second apparatus for increasing the pressure of said liquid flowstream passing through said second conduit section with respect to the pressure of said liquid flowstream passing through said first conduit section.

20. The method set forth in claim 18 wherein:

the volumetric fraction of gas (fg1) is determined from the equation:

$$fg1 = \frac{E2 - E1(1 + fgr) + eg(fgr)}{E2 - E1(P1/P2) + eg(1 - P1/P2)}$$

wherein E1 and E2 are constants related to the microwave transmissivity through said liquid flowstream in said first apparatus and said second apparatus, respectively, fgr is the quantity of gas redissolved into said liquid phase at the pressure in said second apparatus, e.g. is the dielectric constant of the gas, and P1 and P2 are the pressures in said first apparatus and said second apparatus, respectively, at which measurements of microwave transmissivity are measured.

* * * * *

UNITED STATES PATENT AND TRADEMARK OFFICE
CERTIFICATE OF CORRECTION

PATENT NO. : 4,852,395

DATED : Aug. 1, 1989

INVENTOR(S) : Miroslav M. Kolpak

It is certified that error appears in the above-identified patent and that said Letters Patent is hereby corrected as shown below:

Column 11, line 35, delete "the" and insert --- to ---.

Column 12, line 64, delete the colon after "in".

Column 13, line 35, delete "5" and insert --- 5% ---.

Column 14, line 55, delete "e.g." and insert --- eg ---.

Signed and Sealed this

Twelfth Day of June, 1990

Attest:

HARRY F. MANBECK, JR.

Attesting Officer  Commissioner of Patents and Trademarks